United States Patent
Komatsu

(10) Patent No.: US 9,990,828 B2
(45) Date of Patent: Jun. 5, 2018

(54) RESCUE METHOD, RESCUE SYSTEM, WANDERING PERSON CARE METHOD, AND WANDERING PERSON CARE SYSTEM

(71) Applicant: Colan Totte Co., Ltd., Osaka-shi, Osaka (JP)

(72) Inventor: Katsumi Komatsu, Osaka (JP)

(73) Assignee: Colan Totte Co., Ltd., Osaka-shi, Osaka (JP)

(*) Notice: Subject to any disclaimer, the term of this patent is extended or adjusted under 35 U.S.C. 154(b) by 0 days. days.

(21) Appl. No.: 15/309,985

(22) PCT Filed: Jan. 18, 2016

(86) PCT No.: PCT/JP2016/051338
§ 371 (c)(1),
(2) Date: Nov. 9, 2016

(87) PCT Pub. No.: WO2016/189889
PCT Pub. Date: Dec. 1, 2016

(65) Prior Publication Data
US 2018/0096579 A1    Apr. 5, 2018

(30) Foreign Application Priority Data
May 22, 2015 (JP) ................. 2015-104863

(51) Int. Cl.
G08B 23/00    (2006.01)
G08B 21/04    (2006.01)
(Continued)

(52) U.S. Cl.
CPC ....... *G08B 21/0446* (2013.01); *G08B 21/043* (2013.01); *G08B 21/0423* (2013.01);
(Continued)

(58) Field of Classification Search
CPC ............ G08B 21/0446; G08B 21/0423; G08B 21/043; G08B 21/0492; G08B 21/22; A61B 5/1117; G09F 3/005
(Continued)

(56) References Cited

U.S. PATENT DOCUMENTS

| | | | |
|---|---|---|---|
| 5,423,574 A * | 6/1995 | Forte-Pathroff | G09F 3/005 283/74 |
| 6,505,203 B1 * | 1/2003 | Adler | G06Q 30/06 707/999.007 |

(Continued)

FOREIGN PATENT DOCUMENTS

| | | |
|---|---|---|
| CN | 104137137 A | 11/2014 |
| EP | 2657868 A2 | 10/2013 |

(Continued)

OTHER PUBLICATIONS

International Search Report for PCT/JP2016/051338, ISA/JP, dated Feb. 16, 2016.

(Continued)

*Primary Examiner* — Eric M Blount
(74) *Attorney, Agent, or Firm* — Harness, Dickey & Pierce, P.L.C.

(57) ABSTRACT

A rescue method for identifying and rescuing a person in question, the rescue method comprising an operation in which a user wearing a jewelry item having a serial number is encountered and the serial number on the jewelry item is recognized, an operation in which the serial number is conveyed to a data management company that stores the serial number as identification information pertaining to the user, an operation in which the identification information pertaining to the user is conveyed to a rescue organization, and an operation in which a command to rescue the user is issued at the rescue organization.

23 Claims, 9 Drawing Sheets

(51) Int. Cl.
*G08B 21/22* (2006.01)
*A61B 5/11* (2006.01)

(52) U.S. Cl.
CPC ......... *A61B 5/1117* (2013.01); *G08B 21/0492* (2013.01); *G08B 21/22* (2013.01)

(58) Field of Classification Search
USPC ...................... 340/573.1, 573.4; 40/633, 625
See application file for complete search history.

(56) References Cited

U.S. PATENT DOCUMENTS

| | | | | |
|---|---|---|---|---|
| 6,581,073 | B1* | 6/2003 | Adler | G06Q 30/06 707/999.01 |
| 8,600,357 | B2* | 12/2013 | Sterlino | H04M 3/5158 340/539.2 |
| 2002/0113711 | A1* | 8/2002 | Goldstein | G08B 21/028 340/573.4 |
| 2005/0086261 | A1* | 4/2005 | Mammone | G08B 21/0222 707/999.107 |
| 2008/0030346 | A1* | 2/2008 | Despotis | G08B 13/2434 340/572.9 |
| 2010/0090838 | A1* | 4/2010 | Robinson | G08B 27/001 340/573.4 |
| 2014/0070012 | A1 | 3/2014 | Hunt et al. | |
| 2014/0087684 | A1 | 3/2014 | Rodriguez et al. | |

FOREIGN PATENT DOCUMENTS

| | | |
|---|---|---|
| JP | 2001-307264 A | 11/2001 |
| JP | 2007-209322 A | 8/2007 |
| JP | 2008-118256 A | 5/2008 |
| JP | 2010-256964 A | 11/2010 |
| JP | 2013-114270 A | 6/2013 |
| WO | WO-2003009224 A1 | 1/2003 |
| WO | WO-2013/020185 A1 | 2/2013 |

OTHER PUBLICATIONS

Chinese Office Action dated Dec. 21, 2017 in parallel application CN 2016800015517.
European Office Action and Supplementary Search Report dated Feb. 16, 2018 in parallel application EP 2016/0788630.8.

* cited by examiner

RESCUE METHOD, RESCUE SYSTEM, WANDERING PERSON CARE METHOD, AND WANDERING PERSON CARE SYSTEM

CROSS-REFERENCE TO RELATED APPLICATIONS

This application is a 371 U.S. National Stage of International Application No. PCT/JP2016/051338, filed Jan. 18, 2016, which claims the benefit of and priority to Japanese Patent Application No. 2015-104863, filed May 22, 2015. The entire disclosures of both of the above applications are incorporated herein by reference.

TECHNICAL FIELD

The present invention relates to a rescue method, rescue system, wandering person care method, and wandering person care system. In particular, the present invention relates to a method and system for identifying and rescuing a person who has fallen while walking or jogging, and to a wandering person care method and system permitting easy identification of personal information.

BACKGROUND ART

In recent years, together with the ageing of society, there has been increase in the number of elderly people who live alone and in the number of households made up only of elderly people. Likelihood of occurrence of dementia typically increases with increasing age, and in a survey conducted by the Ministry of Health, Labor and Welfare it was found that as of 2013 there were 4,200,000 patients with dementia (including mild cases), with further steep increase therein being anticipated.

More than half of dementia patients receive nursing care at home, and there are many patients who, e.g., when the nursing caregiver is not there, etc., begin to wander about and become lost. At present, there being more than 10,000 wandering persons per year who are the subject of a missing person report, organizational activities are underway to achieve coordination with respective municipalities, police, and so forth. Given such circumstances, the Wanderer Monitoring SOS Network as shown in FIG. 9 exists as a system and network for quickly finding wandering elderly persons.

As shown in FIG. 9, the Wanderer Monitoring SOS Network is a system in which an Elderly Assistance Section is established at a municipality (e.g., at the city or town hall thereof), with police department(s) and SOS Network collaborator(s) working in coordination therewith to search for wandering person(s). Where this system has been introduced, a target who wanders or is thought to be at risk of wandering, or the family (nursing caregiver) thereof, can make application to register in advance for wanderer monitoring, so that when a missing person search request is made, found person information can be quickly communicated by way of a single fax transmission or the like.

Because the wandering person search radius increases as the duration of a wandering episode increases, making search by only family and acquaintances difficult, the Wanderer Monitoring SOS Network plays an important role. In addition, it is expected that this Wanderer Monitoring SOS Network will expand to become a nationwide network.

PRIOR ART REFERENCES

Patent References

PATENT REFERENCE NO. 1: Japanese Patent Application Publication Kokai No. 2008-118256

PATENT REFERENCE NO. 2: Japanese Patent Application Publication Kokai No. 2013-114270

SUMMARY OF INVENTION

Problem to be Solved by Invention

However, despite the high expectations that have existed for the Wanderer Monitoring SOS Network, the reality is that the Wanderer Monitoring SOS Network has failed to deliver results commensurate with what had been expected of it, and the number of municipalities that have introduced the network hardly approaches anything approximating the total number of municipalities that exist nationwide. While there is also the problem of the budget that has been allotted for introduction of the Wanderer Monitoring SOS Network, upon consideration by the present inventor(s) it was found that the Wanderer Monitoring SOS Network has problems such as the following.

It must first be said that because the department (e.g., Elderly Assistance Section) within the municipality in principle operates the Wanderer Monitoring SOS Network only during business hours, it is not available 24 hours per day 365 days per year, and so searches for wandering persons cannot be carried out quickly. Furthermore, public transportation service staff and employees of convenience stores or gasoline stands are envisioned as operators collaborating with the SOS Network, but given the fact that they will be collaborating in searches only to the extent permitted in light of their ordinary duties, it is difficult to expect that they will be able to participate in aggressive search activities.

Moreover, in the case of the Wanderer Monitoring SOS Network, while some municipalities make use of an identification marker in the form of a seal, e.g., one that reads "City of ** No. 1234" or the like, which is affixed to the heal of the shoe to identify the person in question, the first thing that must be said is that this identification marker should be properly affixed to a location on the shoe or the like that will be easily seen. Where said identification marker is not present for reasons such as might be the case when a person is embarrassed to wear said identification marker or when the shoes they are wearing are other than those to which the identification marker is affixed, this makes search extremely difficult because the wandering person must be identified based on information such as what clothes they were wearing at the time, their facial characteristics, and so forth.

Because the Wanderer Monitoring SOS Network is a service that is provided separately by each municipality, in a situation where a wandering person manages to travel as far as a neighboring municipality, regardless of the fact that the person may have been registered in the municipality in which he or she is resident (and regardless of the fact that he or she may be wearing an identification marker), there will be no search in the neighboring municipality.

The present inventor(s) have therefore come to the realization that even if the Wanderer Monitoring SOS Network were provided with an ample budget, and even if it were in operation 24 hours per day 365 days per year, it would still be difficult to carry out search and identification of a wandering person in the context of this system. Moreover, the reality is that budgets are limited and operations cannot be carried out 24 hours per day 365 days per year, meaning that even in situations where a person is lucky enough to be found, it might still be the case that fax transmission does not go smoothly at a time when the service is not in operation; and under circumstances in which there is no limit to the meagerness of the information based on which the person in question is supposed to be identified, it is entirely possible that situations might be encountered in which the family or nursing caregiver cannot be contacted even when the wandering person is being cared for.

In view of this, a strategy might be contemplated in which mobile phone(s) or smartphone(s) are employed instead of the Wanderer Monitoring SOS Network to identify the person in question. In particular, because mobile phones and smartphones may have GPS capability, there would be the advantage that they might also permit identification of location information for the person in question. For example, Patent Reference No. 1 discloses a dementia patient care system that employs a PHS mobile terminal.

However, a method that might utilize a mobile phone or smartphone would have the following problems. The first thing that should be mentioned is the problem of whether a dementia patient would have a mobile phone or smartphone with them every time they went out. Considering that even healthy adults sometimes go out without bringing along their mobile phone or smartphone, it seems likely that a dementia patent who is having a wandering episode might go out without bringing along their mobile phone or smartphone, or that somewhere along the way their mobile phone or the like could be forgotten or lost. Of course, without a mobile phone or the like, the person in question could not be identified. Moreover, with a mobile phone or the like, there is the problem of what happens when the battery runs out. Where the battery of the mobile phone or the like has run out, it will not be possible to identify the person in question.

Note further that while there are cases in which someone (a finder) who finds a dementia patient who is wandering might be able to identify the person in question from the mobile phone or the like which that dementia patient might be carrying, because it is often the case that mobile phones and the like are locked so as to permit protection of personal information, it will not always be possible to identify the person in question from their mobile phone or the like. Furthermore, the psychological reluctance to touch or inspect a mobile phone or the like that belongs to someone else is also relevant.

Another means that might be contemplated is the placement of a GPS terminal or other such transmitter in the clothing or shoes that are worn on a regular basis. However, just because someone is a dementia patient does not mean that they will not object to their location being tracked on a regular basis by a GPS terminal. For this reason, it would not be at unusual for a person to deliberately avoid using clothing or shoes in which a GPS terminal has been placed. Furthermore, while one might consider writing the person's name and contact information on their clothing or on something they possess, one must also keep in mind the dangers that present themselves to a person who goes out in a state in which they are constantly displaying their personal information. That is, more important than whatever benefit might be obtained in reducing wandering, it is necessary to consider the possibility that the person could become a victim of fraud or the like.

Proposed at Patent Reference No. 2 is a web application system that supports a service which provides protection of personal information as well as support at times of emergencies. In accordance with this system, a technique is disclosed that makes it possible for personal information to be protected at ordinary times, but that makes it possible only in times of emergency for an organization that performs emergency support services to announce personal information and to divulge personal information to a medical institution or the like in their capacity as agent. However, to provide this service 365 days per year 24 hours per day, including staff and facilities for implementing emergency support services, would involve enormous expense and require an enormous budget. Considering the constraints that exist with respect to expenses and budget, it would be difficult to popularize this system.

Moreover, the present inventor(s) also investigated the following. In recent years, there has been increase in the number of people who enjoy walking, running, and other such sports. Because walking, running, and so forth is primarily done alone, in the event of occurrence of a seizure (including stroke, heart attack, etc.), accident, or other such emergency situation, it will be necessary to rely on help from someone with whom one is not acquainted. It is often the case that someone who engages in walking, running, or the like may not bring along a driver's license or other such personal identification information (ID card) but may have on their person only a little small change. In such a situation, identification of that person would be extremely difficult.

Furthermore, unlike the situation with a wandering dementia patient, a healthy adult will dislike the fact that his or her location is being identified by a GPS terminal, such that even where someone in the person's family turn ON the GPS functionality, the person in question will have both the ability and the desire to disable that GPS functionality. Moreover, even if the person is carrying a smartphone or the like, this is nearly always locked, meaning that the finder will be unable to see the content of the smartphone belonging to the person who experienced the emergency situation, making it impossible to obtain identification information therefrom.

What is more, even if they are not a wandering dementia patient or someone who enjoys walking, it is often the case that an elderly person will have some medical condition, and so rapid response is desired when a person who has gone out suffers a change in their physical condition or suddenly takes ill. When the person in question is unconscious or is having a convulsion, it is unlikely that the person in question will be able to verbally communicate their personal information.

The present invention was conceived in light of such issues, it being a primary object thereof to provide a rescue method and rescue system, and a wandering person care method and system, permitting easy identification of personal information.

Means for Solving Problem

A rescue method associated with the present invention is a rescue method for identifying and rescuing a person in question that includes an operation in which a user wearing the jewelry item having a serial number is encountered and the serial number on said jewelry item is recognized; an operation in which the serial number is conveyed to a data management company that stores the serial number as identification information pertaining to the user; an operation in which the identification information pertaining to the user is conveyed from the data management company to a rescue organization capable of rescuing the user; and an operation in which a command to rescue the user is issued at the rescue organization.

In a preferred embodiment, the jewelry item at the operation in which the recognition occurs is one species selected from among the group consisting of necklace, bracelet, and anklet; at the operation in which the recognition occurs, the serial number is recognized by a smartphone possessed by the finder who encountered the user; the data management company is a credit card company; and the serial number recognized by the smartphone of the finder is transmitted to the credit card company by the communication network connected to the smartphone.

A preferred embodiment further comprises an operation in which an advertisement of the credit card company is caused to be displayed at a plurality of smartphones connected to the communication network.

In a preferred embodiment, location information pertaining to the user is transmitted to the credit card company based on location information possessed by the smartphone of the finder.

In a preferred embodiment, the serial number is recognized by a camera of the smartphone of the finder; and stored at the smartphone of the finder is a rescue application that transmits the serial number to the credit card company.

In a preferred embodiment, at least one member of the rescue organization is a security company; and an instruction to go to the location of the user is issued to staff of the security company based on user rescue information including the identification information pertaining to the user from the data management company.

In a preferred embodiment, at least one member of the rescue organization is a fire department having an ambulance; and an instruction to go to the location of the user is issued to staff of the fire department based on user rescue information including the identification information pertaining to the user from the data management company.

In a preferred embodiment, the serial number is a two-dimensional barcode.

A rescue system associated with the present invention is a rescue system for identifying and rescuing a person in question that comprises a first database that stores a serial number on a jewelry item as identification information; and a second database that receives user rescue information including the identification information by way of a communication network; wherein the user rescue information includes the identification information and includes location information pertaining to the person in question.

Another rescue system associated with the present invention is a rescue system for identifying and rescuing a person in question that comprises a first database that stores a serial number on a jewelry item as identification information; and a second database that receives user rescue information including the identification information by way of a communication network. The first database is provided at the data management company; the second database is provided at the rescue organization; and the serial number is transmitted to the first database by a mobile communication device.

In a preferred embodiment, the rescue organization is at least one species selected from among the group consisting of fire department, police department, and security company; the user rescue information includes the identification information and includes location information pertaining to the person in question; and incorporated within the second database is rescue programming for issuing a command to rescue the person in question.

In a preferred embodiment, the jewelry item has a form such as will permit wearing thereof by the person in question; and a smartphone application that recognizes the serial number is distributed to a plurality of smartphones by way of the communication network.

A wandering person care method associated with the present invention is a method for identifying and caring for a wandering person that includes an operation in which a wandering person wearing the jewelry item having a serial number is encountered and the serial number on said jewelry item is recognized; an operation in which the serial number is conveyed to a data management company that stores the serial number as identification information pertaining to the wandering person; an operation in which the identification information pertaining to the wandering person is conveyed from the data management company to a rescue organization that will rescue and care for the wandering person; and an operation in which a command to care for and rescue the wandering person is issued at the rescue organization.

In a preferred embodiment, the jewelry item at the operation in which the recognition occurs is one species selected from among the group consisting of necklace, bracelet, and anklet; and the jewelry item is equipped with a catch.

In a preferred embodiment, at the operation in which the recognition occurs, the serial number is recognized by a smartphone possessed by the finder who encountered the wandering person; the data management company is a credit card company; and the serial number recognized by the smartphone of the finder is transmitted to the credit card company by the communication network connected to the smartphone.

A care system associated with the present invention is a care system for identifying and caring for a wandering person that comprises a first database that stores a serial number on a jewelry item as identification information; and a second database that receives user rescue information including the identification information by way of a communication network. The first database is provided at a data management company; the second database is provided at a rescue organization; the serial number is transmitted to the first database by a mobile communication device; the rescue organization is at least one species selected from among the group consisting of fire department, police department, and security company; the user rescue information includes the identification information and includes location information pertaining to the wandering person; and incorporated within the second database is rescue and care programming for issuing a command to rescue and care for the wandering person.

In a preferred embodiment, the jewelry item has a form such as will permit wearing thereof by the person in question; the jewelry item at the operation in which the recognition occurs is one species selected from among the group consisting of necklace, bracelet, and anklet; and a smartphone application that recognizes the serial number is distributed to a plurality of smartphones by way of the communication network.

A program associated with the present invention is a program for identifying and rescuing a person in question that causes execution of a rescue method for identifying and rescuing the person in question. The rescue method may be executed using a rescue system comprising a first database that stores a serial number on a jewelry item as identification information; and a second database that receives user rescue information including the identification information by way of a communication network. The program for identifying and rescuing the person in question is a program that causes a step in which a user wearing the jewelry item having the serial number is encountered and the serial number on said jewelry item is recognized; a step in which the serial number is conveyed to a data management company that stores the serial number as identification information pertaining to the user; a step in which the identification information pertaining to the user is conveyed from the data management company to a rescue organization capable of rescuing the user; and a step in which a command to rescue the user is issued at the rescue organization to be executed in the context of the rescue system. The first database is provided at the data management company; and the second database is provided at the rescue organization.

An application program associated with the present invention is an application program capable of being executed by a mobile communication terminal used in the context of the program for identifying and rescuing the person in question and which is such that, of the steps in the program for identifying and rescuing the person in question, the step in which the serial number of the jewelry item is recognized and the step in which the serial number is conveyed to the data management company are executed by the mobile communication terminal.

Benefit of Invention

In accordance with the present invention, a serial number on a jewelry item worn by a user may be recognized and conveyed to a data management company, as a result of which the person in question may be identified while protecting the personal information of the user; and by thereafter causing the identification information pertaining to that user to be conveyed from the data management company to a rescue organization, a command to rescue the user can be issued at the rescue organization. As a result, it is possible to provide a rescue method and rescue system permitting easy identification of personal information.

Describing this in further detail, with the Wanderer Monitoring SOS Network, it is unrealistic to expect that service could be provided 24 hours per day 365 days per year, and there is the fact that application to register in advance at the municipality (city or town hall) is complicated. Moreover, there are such problems as the fact that the identification marker has to be worn whenever the person goes out, and the fact that search capability becomes ineffective when the person wanders outside of the range of the municipality for which application and registration was carried out.

On the other hand, with the present invention, the serial number on a jewelry item is used as identification marker for the user in question. For reasons related to proof of product authenticity, extended product warranty (e.g., assistance with product operation and/or repair/replacement warranty), and so forth, jewelry items have marked thereon a product number or item number (serial number) such that there is one number per jewelry item; in accordance with the present invention, this serial number is utilized to identify the person in question. Because the serial number itself is marked thereon for the purpose of identifying each individual product item, there is no need to incur the additional separate cost that would accompany introduction of an identification marker for the user in question. In other words, there is no need to carry out application and registration, as well as the administration thereof, mailing of the identification marker to the wandering person, and other such procedures, as is the case with the Wanderer Monitoring SOS Network. In addition, with a serial number on a jewelry item, there is no need to separately affix an identification marker to a shoe or other such object, and because serial numbers are in principle made so as not to come off of jewelry items, serial number management is easy (there is no possibility that the serial number will disappear).

Moreover, where the data management company is the company that sells (or is the company that manufactures) said jewelry item, if that company that sells the jewelry item has a support center that is available 24 hours per day 365 days per year, it will be possible at almost no additional cost to provide business support for a method or system in accordance with the present invention 24 hours per day 365 days per year. And if the company that sells the jewelry item does not have a support center that is available 24 hours per day 365 days per year, a credit card company might be used as the data management company. Because credit card companies have support centers and/or customer service centers that are available 24 hours per day 365 days per year so as to be able to respond to card theft or fraudulent usage incidents and the like and so as to be able to provide customer service for preferred customers, if a credit card company is the data management company at which the serial number of the jewelry item is stored as identification information pertaining to the user, it will be able to provide service(s) 24 hours per day 365 days per year. In particular, if that credit card company is the company that processed the payment at the time that the jewelry item having said serial number was purchased, this has the advantage that it would allow the identification information (e.g., name, address, birth date, etc.) used to process that credit card payment to be used as identification information for the user. In other words, with the Wanderer Monitoring SOS Network, identification information (e.g., name, address, birth date, and/or other information or the like necessary for identification of the person in question) would have to be submitted to the municipality for application and registration, and the municipality would have to enter and manage that information, incurring substantial inconvenience and cost; however, in accordance with the present invention, because credit card company payment information (or user information or purchase information from the company that sold the jewelry item) may be utilized, it is possible to cause input and administration of identification information for the user to be greatly simplified or to be automated.

Furthermore, in accordance with the present invention, because a serial number on a jewelry item is used, the problem of depleted batteries does not occur. Moreover, because GPS functionality is not being used to constantly monitor the location of the person in question, this reduces stress on the person in question. In addition, because the person in question can purchase the jewelry item that he or she likes, this will increase the likelihood that it will be worn on a regular basis, as a result of which it will be possible to avoid the problem whereby people do not want to wear the registered identification seal provided by the municipality because it is perceived as unattractive. In addition, the present invention obviates the need to display the name, address, or other such personal information on the clothing, shoes, or the like of the person in question. In other words, the serial number of the jewelry item is by itself a meaningless number, and because personal information is stored internally at a credit card company (or a company that sells the jewelry item), at which the level of security is extremely high, the probability of abuse of personal information is extremely low as compared with the situation in which the name, address, or other such personal information is displayed on the clothing, shoes, or the like of the person in question.

In addition, the object of the Wanderer Monitoring SOS Network is identification and care of elderly wandering persons; expansion of coverage to healthy adults is either not contemplated, or were it to be expanded to cover adults it would require an enormous budget. The present invention is capable of accommodating not only wandering persons but also users who suffer an accident, seizure, or the like while engaged in an activity such as running or the like; and with respect to the manner of its introduction, all that a user need do is purchase and wear a jewelry item that has a serial

EMBODIMENTS FOR CARRYING OUT INVENTION

Figure 1:
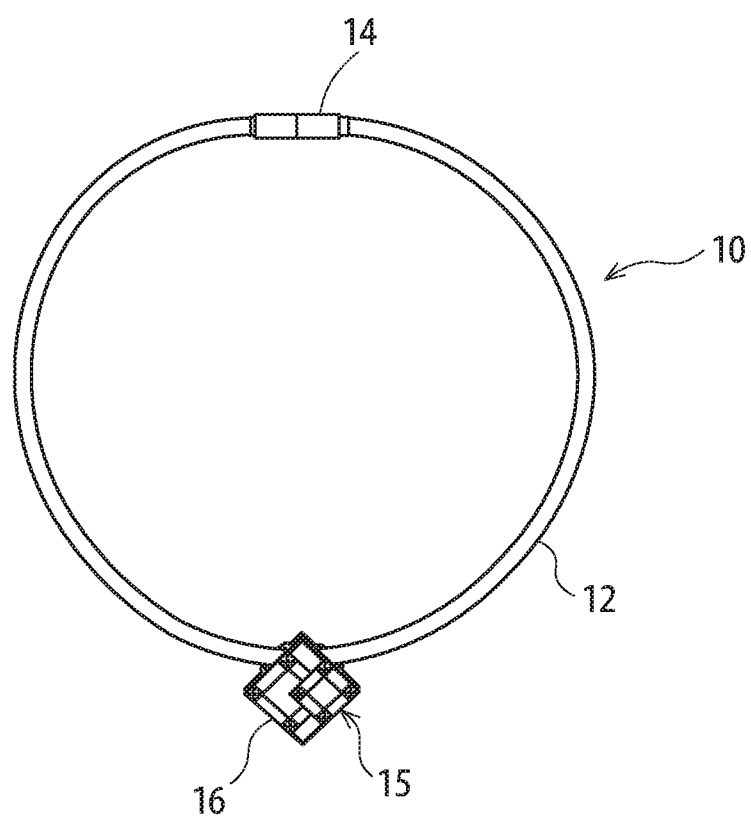
FIG. 1 Drawing showing in schematic fashion a jewelry item (necklace) 10 associated with an embodiment of the present invention.

The present inventor(s) considered for some time how to address the problem of the problem of wandering persons who are dementia patients, the number of whom grow greater with each passing year, as well as the problem of seizures and accidents which may suddenly befall even healthy adults when they are engaged in activities such as running or the like. While the "Wanderer Monitoring SOS Network" advocated by the national government and public-sector organizations is one possible means, the present inventor(s) reached the conclusion that this would be difficult to operate in a manner that would be both low in cost and convenient from the standpoint of the user. The present inventor(s) also considered the possibility of making use of the GPS functionality of mobile phones and smartphones, but these would entail problems whose fundamental nature makes them difficult to solve, such as the problem of the privacy of the person in question's location information, the problem of batteries that become depleted, and so forth. After pondering in this fashion for some time, the idea of using the serial number of a jewelry item then occurred to the present inventor(s), but even if the serial number of a jewelry item could be cleverly used to identify the person in question, there would still be the problem of the cost to manage the input and administration of registration information for the person(s) in question, and the additional difficulty of providing service 24 hours per day 365 days per year. However, upon realizing that this difficulty could be overcome by enlisting the assistance of the company of the credit card with which the jewelry item was purchased, the present inventor(s) arrived at the present invention.

Preferred embodiments of the present invention are described below with reference to the drawings. In the drawings that follow, for brevity of description, members and parts possessing identical function are assigned identical reference numerals, and duplicative description thereof may be omitted or abbreviated. Furthermore, note that dimensions (lengths, widths, thicknesses, etc.) in the respective drawings do not necessarily accurately reflect actual dimensions. Furthermore, matters that are not included among the items specifically mentioned in the present specification but that would be necessary to carry out the present invention are design items that one of skill in the art would be capable of apprehending based on the conventional art pertaining to the field in question. The present invention may be carried out based on the content that is disclosed in the present specification and drawings and based on common technical knowledge pertaining to the field in question. In addition, the present invention is not to be limited by the following embodiments.

FIG. 1 is a drawing showing the constitution of a jewelry item 10 associated with an embodiment of the present invention. Jewelry item 10 shown in FIG. 1 is a necklace. Necklace 10 shown in the drawing comprises linear member (wire portion) 12 which goes about the neck, connector 14 which connects/disengages linear member 12, and pendant (ornamental member) 16 which is attached to linear member 12. Pendant 16 is marked with a serial number 15 that is individually assigned so that there is one for each necklace (jewelry item) 10.

In the present embodiment, serial number 15 is marked on pendant 16 at an inconspicuous location (back, side, etc.) thereof. Serial number 15 may be marked on pendant 16 after the fashion of an engraving, or may printed thereon by means of a laser, or may be affixed thereto after the fashion of a seal. In accordance with its purpose based on the application(s) for which jewelry item 10 may be used, serial number 15 of the present embodiment is marked thereon to prove that jewelry item 10 is an authentic product, but there is no objection to using it for other purpose(s) (repair, exchange, services provided during warranty period, and/or other such purpose(s)). Serial number 15 may be marked on respective necklaces which might be manufactured in large quantities after the fashion of a number issued in consecutive fashion, or may be marked thereon in random fashion as a definitive measure for addressing the problem of pirated goods.

Note that serial number 15 may be marked on pendant 16 at a conspicuous location (front, etc.) thereof, and there is no objection to performing marking at a part (e.g., wire 12 or connector 14) other than pendant 16. In addition, serial number 15 is not limited to numbers, letters of the alphabet, and other such characters, it being possible to employ a serial number 15 which is after the fashion of a barcode (including two-dimensional barcodes, QR codes (registered trademark), etc.). That is, serial number 15 is a marker for identifying each individual necklace (jewelry item) 10, and is not limited to numbers (numeric symbols). Besides barcodes, there is no objection to employment of a marker for individual identification such as an RFID tag or other such semiconductor integrated circuit (e.g., FeliCa chip, μ-chip, etc.).

Necklace 10 of the present embodiment may be a magnetic necklace. Where this is the case, one or more magnets may be arranged at wire 12 and/or connector 14. In accordance with the constitution of necklace 10 in the example shown in the drawing, a pair of magnets are arranged such that an S pole and an N pole are arranged so as to be mutually adjacent but separated by some distance from each other. Note that there is no objection to a situation in which magnet(s) are arranged at pendant 16.

Figure 2:
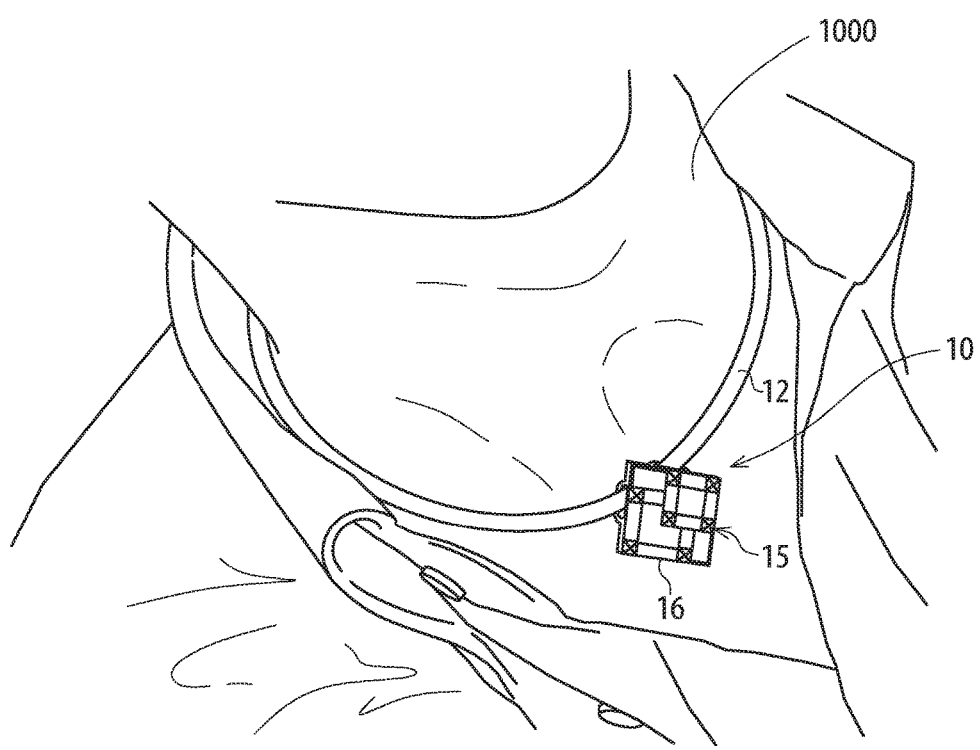
FIG. 2 Drawing of at time when jewelry item (necklace) 10 is worn by a user 1000.

FIG. 2 shows a situation in which user 1000 is wearing necklace 10. The situation shown in FIG. 2 shows user 1000 experiencing an abnormality in which he or she needs help due to having fallen as a result of suddenly becoming unable to move because of a sudden seizure that occurred while he or she was running.

In the situation shown in FIG. 2, if the person in question 1000 recovered by himself or herself after a short time or if there was an acquaintance nearby, because mobile phone or smartphone which they might be carrying could be used to call an ambulance, the worst-case scenario might be avoided. But when the person in question cannot recover by himself or herself and there is no acquaintance nearby, although someone in the area thereabout might be inspired to help said person in question 1000, they would be unable to ascertain who the person in question is if that person in question 1000 did not have with them a driver's license or other such personal identification information (ID card). And although that finder might call an ambulance, the measures that might be taken in the situation in which it is not possible to ascertain who the person in question is versus the situation in which it is possible to ascertain who the person in question is are completely different.

And if FIG. 2 is interpreted as showing the situation that might exist when a wandering dementia patient is being cared for, while there might not be any need to call an ambulance or the like, the state of being unable to ascertain who the person in question is might continue, despite the fact that the person in question might be brought to the police, if that person in question 1000 did not have with them a driver's license or the like. There are cases in which a person is rescued in a state in which their clothes are in tatters, they have no items in their possession, and they do not even know their own name or address, and since the person in question cannot be identified merely based on their face or general appearance, it may be quite some time (e.g., several months) that they remain in the state that they were in when someone took them into their care without it being possible to contact their family or acquaintances.

Figure 3:
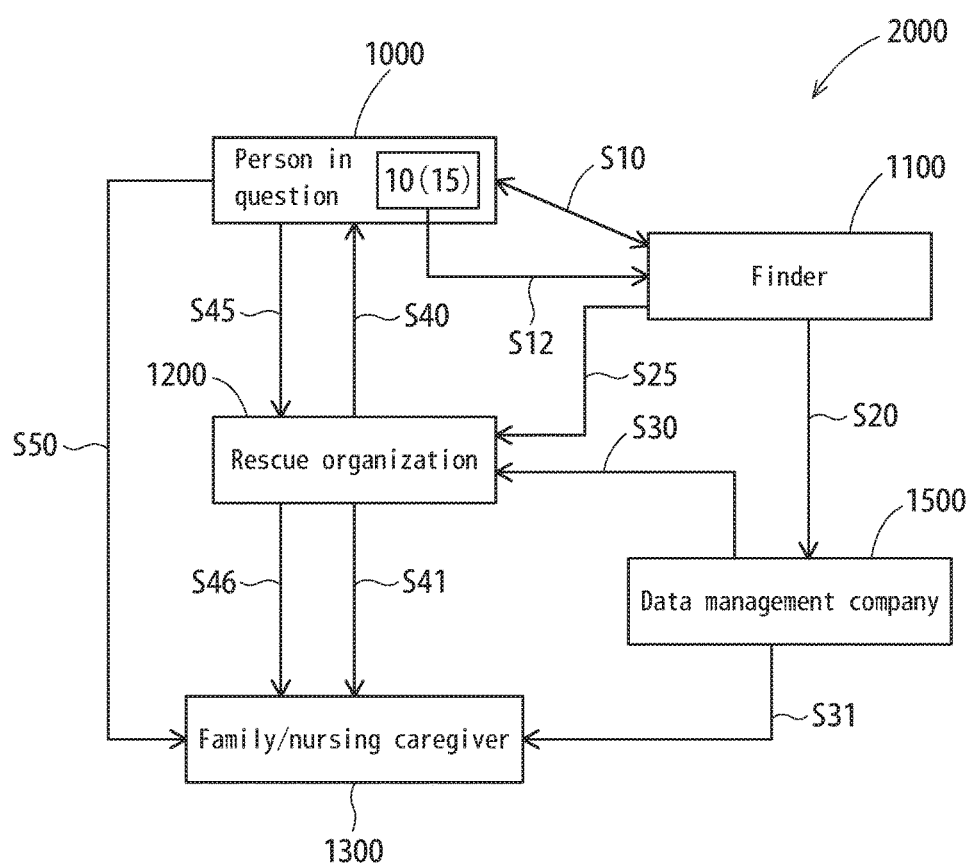
FIG. 3 Block diagram for explaining a rescue method associated with an embodiment of the present invention.
Figure 4:
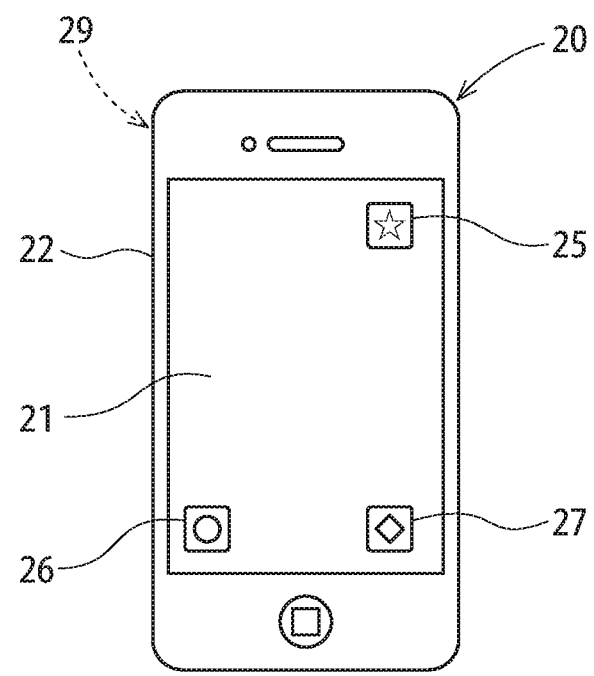
FIG. 4 Drawing showing a mobile communication terminal (smartphone) 20 associated with an embodiment of the present invention.

It is at such a time that the rescue method and/or rescue system associated with an embodiment of the present invention might be employed to facilitate identification of the person in question and to cause any rescue treatment taking place thereafter to proceed smoothly. FIG. 3 is a block diagram for explaining the rescue method of the present embodiment. FIG. 4 is a mobile communication terminal (smartphone) 20 used in the rescue method of the present embodiment.

Indicated at the constitution shown in FIG. 3 are the person in question (user) 1000 who has on his or her person jewelry item 10 having serial number 15, finder 1100, rescue organization 1200, family/nursing caregiver 1300, and data management company 1500. What the person in question (user) 1000 might look like when he or she is wearing jewelry item 10 is shown, for example, at FIG. 2.

"Finder 1100" shown in FIG. 3 might have with them a mobile communication terminal 20 such as that which is for example shown in FIG. 4. Mobile communication terminal 20 shown in FIG. 4 is a so-called smartphone (e.g., an iPhone (registered trademark) manufactured by Apple Inc. or a smartphone running the Android OS (any of the various types of Android smartphones)). A smartphone is a multifunctional mobile phone, being equipped with telephone functionality and Internet communication functionality; not only does it have telephone functionality, but it is also capable of carrying out information management, modification, transmission, and so forth.

Smartphone 20 shown in FIG. 4 is equipped with display 21 and case 22. The side on which display 21 is located is the front; at the back, which is on the side opposite thereto, is located a camera (not shown) 29, it being possible to use this camera 29 capture images. Images captured with this camera 29 may be transmitted by way of the Internet or such images may be analyzed and subjected to information processing.

Smartphone 20 is capable of causing operation of certain programs (applications), icons 25 through 27 for such applications (sometimes also referred to as "apps") being displayed at display 21. Display 21 may be a touchpanel display (liquid crystal display or organic EL display) which permits applications to be launched when icons (25, 26, 27) on the display 21 are touched.

First icon 25 shown in FIG. 4 is a "rescue app icon" permitting execution of a rescue method in accordance with the present embodiment. Second icon 26 is an icon for an app (or website) managed/hosted by a company that sells jewelry item 10. Third icon 27 is an icon for an app (or website) managed/hosted by the company of the credit card used to make payment when jewelry item 10 was purchased.

"Data management company 1500" shown in FIG. 3 is a company that stores serial number 15 of jewelry item 10 as identification information pertaining to user 1000. In the example of the present embodiment, data management company 1500 is the company of the credit card used to pay for purchase of jewelry item 10 (or a company that sells jewelry item 10). Data management company 1500 is typically a for-profit entity (Kabushiki Kaisha, LLC, LLP, etc.), but there is no objection to its being a nonprofit organization (NPO), and it does not matter whether or not it has corporate status. While data management company 1500 of the present embodiment is an entity which is a Kabushiki Kaisha that has corporate status, there is no objection to its being a sole proprietorship or to its being an cooperative organization that does not have corporate status. Data management company 1500 may also in some cases be an organization or entity such as the national government or a government agency, or a regional public-sector organization.

In a preferred embodiment, "rescue organization 1200" shown in FIG. 3 might for example be—if it is in the public sector—a fire department, police department, city or town hall, or the like. If it is in the private sector, it might be a security company (e.g., a residential security company). Note that it is possible to for the scope of application of the rescue method of the present embodiment to be such that rescue organization 1200 may include a convenience store, gasoline stand, taxi company, railroad company, bus company, and/or the like.

"Family/nursing caregiver 1300" shown in FIG. 3 is typically the family of user 1000. In the context of taking care of a wandering person, where there is no family to look after the person but there is a nursing caregiver, "family/nursing caregiver 1300" would be the nursing caregiver who looks after user 1000. Note that even where there is family, a friend or acquaintance may be designated as contact information for "family/nursing caregiver 1300".

In accordance with the rescue method of the present embodiment, as shown in FIG. 3, the first thing to be said is that finder 1100 encounters user 1000 who has on his or her person jewelry item 10 having serial number 15, upon which finder 1100 becomes aware of serial number 15 (step S10). More specifically, serial number 15 is such that when finder 1100 touches jewelry item 10, discovering the place where serial number 15 is located makes it possible for it to be read therefrom. Furthermore, this serial number 15 is such that camera 29 of smartphone 20 of finder 1100 can be used to take a picture of it.

Next, finder 1100 communicates serial number 15 of which he or she has become aware to data management company 1500 (step S20). More specifically, finder 1100 uses the telephone functionality of smartphone 20 to telephone the contact person at data management company 1500 and verbally communicate to them the serial number 15. The telephone number of the contact person at data management company 1500 can be learned by using smartphone 20 to go to the website of the company that sells jewelry item 10. In addition, using one's finger to touch the corresponding telephone number displayed at display 21 of smartphone 20 permits a telephone call to be made directly to that contact person 24 hours per day 365 days per year. When the contact person answers the telephone, finder 1100 verbally communicates serial number 15, and the current location and status (health status, clothing, etc.) of user 1000. Finder 1100 may thereafter while talking on the telephone receive instructions from the operator with whom he or she is talking.

Furthermore, where a "rescue app (25)" permitting execution of a rescue method in accordance with the present embodiment has been installed on smartphone 20 of finder 1100, the following may be carried out. When finder 1100 uses camera 29 of smartphone 20 to capture an image of serial number 15, "rescue app (25)" may execute operations whereby the analyzed serial number 15 is read therefrom, and may even go so far as to place the telephone call to the contact person at data management company 1500. More specifically, when rescue app icon 25 is pressed to launch the rescue app and camera 29 is used to capture an image, rescue app (25) thereafter uses the information processing functionality of smartphone 20 to automatically analyze the image and transmit serial number 15 to data management company 1500, and to telephone data management company 1500. Furthermore, if smartphone 20 of finder 1100 has GPS functionality, location information pursuant as determined by such GPS functionality might be transmitted to data management company 1500.

Where rescue app (25) is installed, serial number 15 may be not only alphanumeric characters such as can be read by a human being but may also be a barcode or two-dimensional barcode. Where smartphone 20 is capable of detecting RFID tags (RFID chips), there is no objection to employment of a constitution in which the RFID tag is used for a serial number 15, such that when smartphone 20 is brought near thereto, rescue app (25) reads the information (serial number 15) from the RFID tag.

Next, data management company 1500, after receiving serial number 15 which has been communicated thereto by finder 1100, identifies identification information (name, sex, address, telephone number, birth date, etc.) pertaining to user 1000. In addition, that identification information is communicated to rescue organization 1200 (step S30).

In the event that serial number 15 is verbally communicated thereto, the operator who is the contact person at data management company 1500 might input that serial number 15 by way of a terminal (keyboard) to access a database at which identification information is stored, and identify the identification information.

Or where serial number 15 is transmitted thereto by rescue app (25) of smartphone 20, the data which has been transmitted thereto might be used to access a database at which identification information is stored so as to permit identification of the identification information. Where this is the case, it will be possible to eliminate the procedure involving input at a terminal by an operator. Furthermore, where the data transmitted by rescue app (25) includes location information, that location information may also be utilized.

Then, at rescue organization 1200, based on identification information communicated thereto from data management company 1500, a command to rescue user 1000 might be issued. At rescue organization 1200, upon receiving the information (information using telephone, fax, electronic mail, online data transmission, or the like) from data management company 1500, the rescue command might be verbally communicated to the person responsible within rescue organization 1200.

Note that where the computer information system at rescue organization 1200 is capable of automatically processing information in online data transmissions from data management company 1500, the constitution might be such as to permit automatic control to be carried out to the point at which a command to rescue user 1000 is issued. In addition, the constitution may be such that information from rescue app (25) is utilized, the information being automatically processed by both data management company 1500 and rescue organization 1200, to the point at which a command to rescue user 1000 is issued.

After the rescue command has been issued, the person responsible (fireman, police officer, security company staff, etc.) at rescue organization 1200 goes to the location of the person in question 1000 (step S40). Rescue organization 1200 may communicate the fact that they are going to the location of the person in question 1000 pursuant to the rescue service (the rescue method/system of the present embodiment) to which user 1000 is subscribed (step S41).

Note that where finder 1100 who encounters user 1000 dials 119 to directly telephone a fire department (1200) (step S25), data management company 1500 may send the identification information to that fire department (1200). Furthermore, data management company 1500 may contact rescue organization 1200 (step S30), and may communicate to family/nursing caregiver 1300 the fact that notification has been received from finder 1100 who encountered user 1000 (step S31).

When the person responsible at rescue organization 1200 arrives at the location of user 1000, that person responsible contacts rescue organization 1200 (step S45). Upon being so contacted, rescue organization 1200 communicates to family/nursing caregiver 1300 the fact that the person in question is being cared for (step S46). User 1000 then, together with the person responsible from rescue organization 1200, goes to the location of family/nursing caregiver 1300 (step S50). Depending on the situation, user 1000 might go to a hospital so he or she can receive medical treatment or an examination.

While various modifications may moreover be made to the techniques described above, a rescue method associated with the present embodiment makes it possible for identification information to be easily identified, and for the person in question to be rescued, merely due to the fact that the user 1000 has in his or her possession a jewelry item 10 having a serial number 15.

Figure 5:
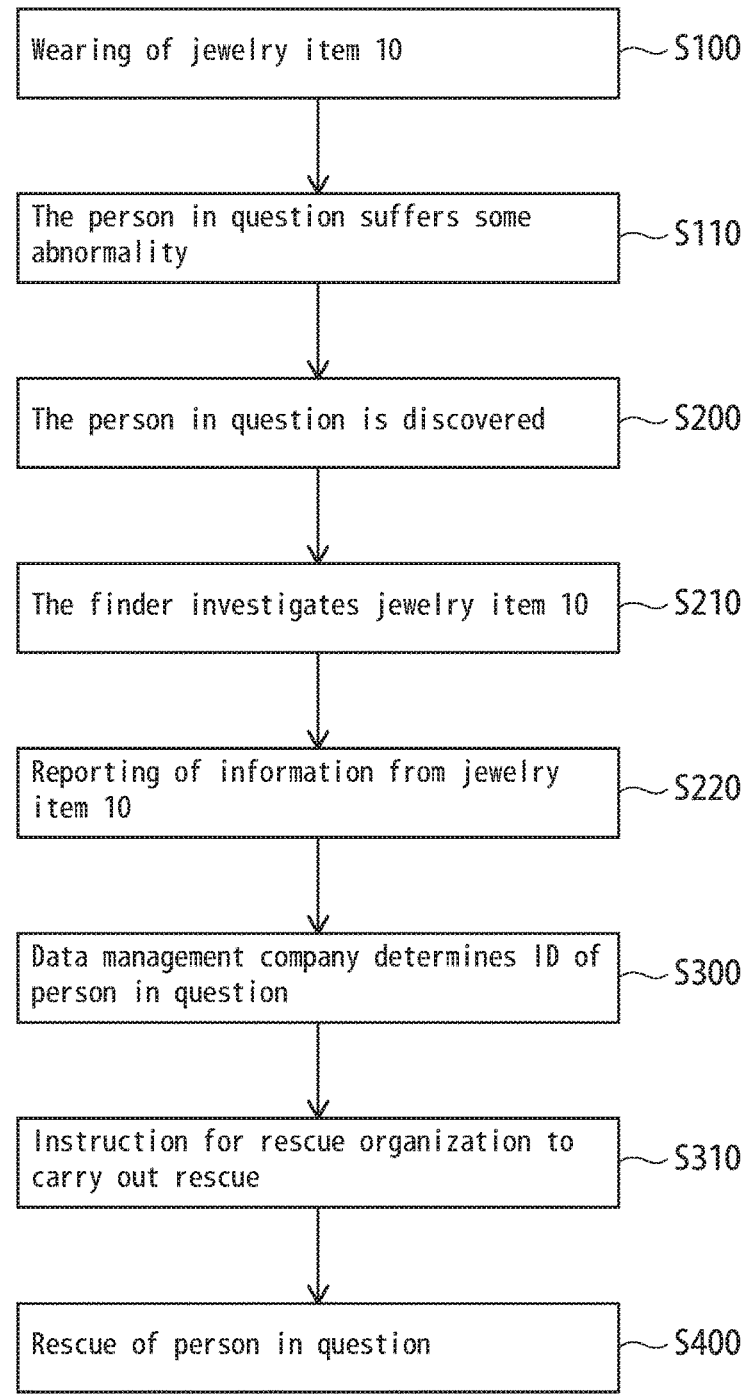
FIG. 5 Flowchart for explaining a rescue method associated with an embodiment of the present invention.
Figure 6:
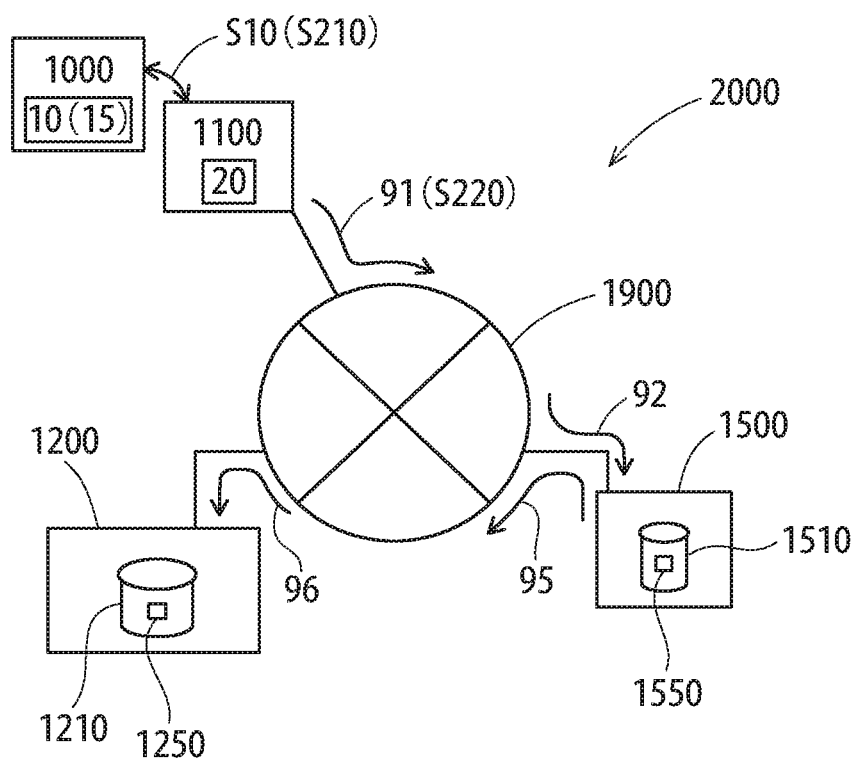
FIG. 6 Drawing for explaining a rescue system associated with an embodiment of the present invention.

Next, with additional reference to FIG. 5 and FIG. 6, an example of a rescue method/system in accordance with the present embodiment will be described in further detail. FIG. 5 is a flowchart for explaining the rescue method of the present embodiment. FIG. 6 is a system diagram for explaining rescue system 2000 in accordance with the present embodiment.

Exemplary rescue system 2000 shown in FIG. 6 will first be briefly described. At rescue system 2000 shown in FIG.

6, smartphone 20 of finder 1100 is connected to communication network 1900. Communication network 1900 is an Internet network (or in some cases may be a telephone network). Data management company 1500 and rescue organization 1200 are connected to communication network 1900 in information network fashion.

Provided at data management company 1500 is a first database (identification information database) 1510. Identification information database 1510 stores serial number 15 in association with identification information 1550. Identification information 1550 is name, sex, address, telephone number, birth date, and so forth, and basically corresponds to information required to make a credit card payment. Note that at the option of user 1000 this identification information 1550 may also include blood type, height, weight, medical history, and/or other such health information. Where identification information 1550 includes health information, this will make it possible to convey this information all the more quickly to an ambulance and/or hospital.

Although identification information database 1510 is connected to communication network 1900, it is protected by sophisticated security. The only person(s) who can access identification information database 1510 are certain person(s) within data management company 1500 who have elevated access privileges. Note that identification information database 1510 stores a multiplicity of sets of identification information 1550, each respective set of identification information 1550 being associated with a single serial number 15.

Note that so long as sophisticated security has been implemented thereat, there is no objection to causing identification information database 1510 to be arranged at location(s) outside of data management company 1500. Furthermore, there is no objection to employment of a plurality of identification information databases 1510 that are mutually managed as backup(s) in the case of disaster. Moreover, there is no objection to employment of a single identification information database 1510 that is managed by a plurality of data management companies 1500. There is no objection to causing backup database(s) for said single identification information database 1510 to be arranged at location(s) outside of data management company 1500.

Provided at rescue organization 1200 is a second database (user rescue database) 1210. User rescue database 1210 may receive information which is transmitted thereto from data management company 1500 (identification information database 1510) by way of communication network 1900. More specifically, user rescue database 1210 receive user rescue information which includes identification information 1550.

In a constitution in accordance with the present embodiment, user rescue database 1210 stores programming (rescue command programming) 1250 that processes user rescue information (1550) and causes a rescue command to be issued to the person responsible within rescue organization 1200. When user rescue information (1550) is received, rescue command programming 1250 becomes active, and a rescue command is transmitted to the person responsible at rescue organization 1200. The person responsible at rescue organization 1200 examines identification information 1550 and location information at a computer terminal within rescue organization 1200 or at mobile terminal(s) (e.g., smartphone(s)) of the respective person(s) responsible, and goes to rescue and care for user 1000.

When rescue organization 1200 is a public agency (fire department or police department), it is possible to imagine situations in which user rescue database 1210 which stores rescue command programming 1250 cannot be installed thereat. In such a situation, the person responsible (operator) at data management company 1500 might use a telephone network 1900 to contact rescue organization 1200. In such a situation, a telephone may be used to establish verbal communication, or a fax transmission might be used to convey identification information 1550. Note that where communication network 1900 is the Internet (optical fiber line or other such digital line) it may be usable as a telephone network (optical fiber telephone). Furthermore, user rescue information which includes identification information 1550 might be transmitted/received as data in the form of online transmission(s), and the rescue command might be verbally spoken within rescue organization 1200.

When rescue organization 1200 is a private-sector company (security company), it is preferred that user rescue database 1210 which stores rescue command programming 1250 be installed thereat. This will make it possible for the portion from the smartphone 20 of finder 1100 to the terminal (computer terminal or mobile terminal) of the person responsible at the security company (e.g., a residential security company) to be connected in integral and information network fashion so that operations can be carried out efficiently.

First database 1510 and second database 1210 of the present embodiment may comprise hard drive(s) (HDD). More specifically, these are storage media at server(s) which is/are connected to communication network 1900. But note that there is no objection to a situation in which first database 1510 and second database 1210 are storage media (hard drive(s) or other such storage device(s)) at cloud computer(s). Furthermore, storage media is not limited to magnetic storage media such as hard drive(s) (HDD), there being no objection to employment of other storage media such as optical storage media, magnetooptical storage media, semiconductor storage media (solid state drive: SSD), and/or the like.

Note that because the program for identifying identification information 1550 using serial number 15 and the program for storing data within first database 1510, and the program for transmitting and receiving of data by way of communication network 1900 and the rescue command programming 1250 within second database 1210 and so forth are not major features of embodiment(s) of the present invention, these will be omitted in the interest of achieving a more concise understanding of the technical content. Such art is capable of being implemented/practiced (carried out) based on common technical knowledge pertaining to the information and communication fields of art. Furthermore, Internet-related art (including website display and advertisement display functionality), camera image capture art, image information processing art, application execution art (including rescue app 25), and telephone/communication art at smartphone 20 will similarly be omitted in the interest of achieving a more concise understanding of the technical content. Such art is capable of being implemented/practiced (carried out) based on common technical knowledge pertaining to the smartphone field of art.

With repeated reference to FIG. 5, an example of a rescue method in accordance with the present embodiment will be described. User 1000 first, at the start, purchases jewelry item (e.g., necklace) 10. If user 1000 uses a credit card to make payment during purchase of jewelry item 10, serial number 15 of jewelry item 10 is stored in the form of information (identification information) 1550 pertaining to that credit card at identification information database 1510.

Where desired by user 1000 in a situation in which user 1000 possesses a smartphone 20, a "rescue app (25)" permitting execution of a rescue method in accordance with the present embodiment may be downloaded by user 1000 so as to cause display of an icon 25 for "rescue app" at said smartphone 20. Or where desired by user 1000, the "rescue app" (25) might be automatically uploaded to said smartphone 20. As a result of the foregoing, in the event that the user 1000 who makes the purchase becomes a finder 1100, this will make it possible to simply and quickly execute the rescue method of the present embodiment.

Furthermore, where desired by user 1000, program(s) that display icon 27 for an app (or website display) managed/hosted by the company of the credit card used to make payment when jewelry item 10 was purchased and icon 26 for an app (or website display) managed/hosted by the company that sells jewelry item 10 may be downloaded thereto by user 1000 or may be automatically uploaded thereto. This will make it possible for new information from the company that sells jewelry item 10 and the credit card company to be conveyed to user 1000, which actions will, as a result, lead to popularization of the rescue method of the present embodiment. If the rescue method of the present embodiment become popular among a large number of people, it will to that extent increase the likelihood that user 1000 will be rescued by someone when he or she is involved in an abnormal situation, permitting improvement in rescue effectiveness.

So that as many as possible might be aware of and share "rescue app" (25), it is therefore preferred to have user 1000 download onto smartphone 20 a program that will facilitate popularization of "rescue app" (25) on social network(s) (SNS); or to employ a constitution which is such that, where desired by user 1000, such a program is automatically uploaded thereto. Note that the "rescue app" (25) or other such installation program might, for example, be stored at first database 1510; however, there is no limitation hereto, it being possible for this to be stored on storage media at any desired server to which Internet network 1900 is connected.

In addition, it is possible to cause advertisements of the credit card company to be displayed at smartphone 20. More specifically, advertisements of the company of the credit card used when jewelry item 10 was purchased may be caused to be displayed at smartphone 20 of user 1000. Moreover, a system (e.g., advertising functionality that operates by way of an SNS system) may be adopted which is such as to permit these to also be displayed on smartphones 20 of acquaintances of that user 1000. Furthermore, it may also be the case that advertisements of the credit card company can be periodically displayed at smartphone(s) 20 of user(s) 1000 who have installed "rescue app" (25). Note that it is also possible to employ a constitution in which not only advertisements of the credit card company but also advertisements of other company or companies (e.g., companies that sell jewelry items 10, residential security companies, sponsoring companies, event-hosting companies, or any other desired companies or organizations (including city or town halls, fire departments, and/or other such public service organizations) and/or the like) are displayed. Note that the installation program for causing display of said advertisements might, for example, be stored at first database 1510; however, there is no limitation hereto, it being possible for this to be stored on storage media at any desired server to which Internet network 1900 is connected.

Note that it will not always be the case that all purchasers of jewelry item 10 will want services that make use of the rescue method of the present embodiment. Operations are therefore carried out so that users 1000 who want said service(s) are able to make use of such service(s) from the time of purchase of jewelry item 10; however, for users 1000 who do not desire start of service(s), serial number 15 is, first, at the time of purchase, associated with credit card information (identification information) 1550 and stored at identification information database 1510, with nothing more being done. In addition, operations are such, if and when service(s) are started, so as to obviate the need for again carrying out application procedures with respect to identification information, use of said service(s) based on combination of the credit card information (identification information) and serial number 15 is made possible. Note that because it may be the case that the telephone number that the person in question registered at the start of service(s) might be only a mobile telephone number and not a home (family) telephone number, it is preferred that user 1000 enter a family/nursing caregiver 1300 that will serve as his or her contact information.

Furthermore, where a need arises to make a change to identification information, a technique might be employed in which the change is made automatically in linked fashion with a change in credit card information (identification information), and/or a technique might be employed in which user 1000 launches "rescue app" (25) and uses this to manually change the identification information. Note that instead of doing this by way of "rescue app" (25) at smartphone 20, a constitution might be adopted in which user 1000 uses a PC (personal computer) terminal to go to the website of the company that sells jewelry item 10, and once there, is able to make the change from an identification information link within that website.

Next, user 1000 wears the jewelry item 10 that he or she purchased (step S100). As described above, mutual association of serial number 15 of jewelry item 10 and identification information 1550 employing credit card information is already completed.

Here, the constitution may be such that when the person wearing jewelry item 10 suffers from dementia and is thought to be at risk of wandering, jewelry item 10 is such that it cannot be removed by the person in question (person suffering from dementia). For example, a constitution might be adopted such that a certain amount of difficulty is involved (e.g., a switch-like structure to prevent it from being removably fastened or an engaging structure to prevent it from being removably fastened) in releasing the catch (connector) 14 of jewelry item 10 shown in FIG. 1. Constitution would be such that the family/nursing caregiver could understand that removably fastened structure and disengage it, but the person in question (person suffering from dementia) could not easily disengage it. By so doing, the person suffering from dementia would no longer be able to discard jewelry item 10 whenever they liked, which would be reassuring to the family and so forth.

Next, the person in question (user) 1000 suffers some abnormality (step S110). What is meant by an abnormality is that user 1000 suffers a seizure, accident, sudden illness, wandering episode, or the like, at which time he or she is in a state other than his or her usual conscious self. More specifically, this might refer to a state in which user 1000 has fallen, is unable to ask for help from other persons thereabout, at which time user 1000 might be unable to say his or her identification information (name, address, etc.).

Next, the person in question (user) 1000 is discovered (step S200). More specifically, at this stage, finder 1100, who was near the person in question 1000, becomes aware of the fact that the person in question 1000 is experiencing an abnormality, and approaches him or her.

Next is the stage at which the person in question 1000 makes no reply to any attempt by finder 1100 to determine who he or she is, at which time finder 1100 investigates the jewelry item 10 which the person in question 1000 is wearing (step S210). While it is preferred that finder 1100 had previously learned about the rescue method of the present embodiment, it would be good if finder 1100 were to then and there investigate by doing a search via the Internet or the like and come to understand that identification as well as rescue of the person in question can be accomplished through use of the rescue method of the present embodiment.

Notification is thereafter made with respect to the information at jewelry item 10 (step S220). More specifically, finder 1100 finds serial number 15 on serial number 15, and transmits that serial number 15 to data management company 1500 (see arrow 91 and arrow 92 at FIG. 6).

Finder 1100 may use the telephone functionality of his or her own smartphone 20 to convey serial number 15 to data management company 1500. Or "rescue app" (25) might be downloaded to smartphone 20, and this might be used to convey serial number 15 thereto. Note that there is no objection to a situation in which finder 1100 discovers that someone nearby has a smartphone 20 on which "rescue app" (25) is installed, and uses that.

Next, data management company 1500 determines the identification information (ID) of the person in question (user) 1000 based on the serial number 15 that was sent thereto (step S300). More specifically, identification information 1550 within identification information database 1510 is determined based on serial number 15. Because identification information 1550 includes name, sex, address, telephone number, and birth date, it is sufficient for identification of the person in question. Furthermore, location information of user 1000 (location information of finder 1100) is obtained from finder 1100. Said location information may be verbally communicated thereto by telephone from finder 1100, or may be obtained from GPS data at smartphone 20 by way of "rescue app" (25).

Next, data management company 1500 issues a rescue instruction to rescue organization 1200 (step S310). More specifically, data management company 1500 transmits identification information 1550 including location information to rescue organization 1200 by way of communication network (Internet network) 1900 (see arrows 95 and 96 at FIG. 6). If rescue organization 1200 does not have second database 1210, telephone network 1900 is used to communicate this by telephone/fax to rescue organization 1200.

Rescue organization 1200 then issues a rescue command and goes to rescue the person in question (step S400). A specific example of the content of rescue operations is as described with reference to FIG. 3. The foregoing procedure makes it possible to achieve a rescue method and rescue system permitting easy identification of personal information.

In accordance with the technique of the present embodiment, serial number 15 at jewelry item 10 on the person of user 1000 is noticed and is communicated to data management company 1500. In accordance herewith, it is possible to identify user 1000 while protecting the personal information of the person in question 1000, following which communication of identification information 1550 pertaining to that user from data management company 1500 to rescue organization 1200 makes it possible for a command to rescue user 1000 to be issued at rescue organization 1200. As a result, it is possible to achieve a rescue method and rescue system permitting easy identification of personal information.

Figure 9:
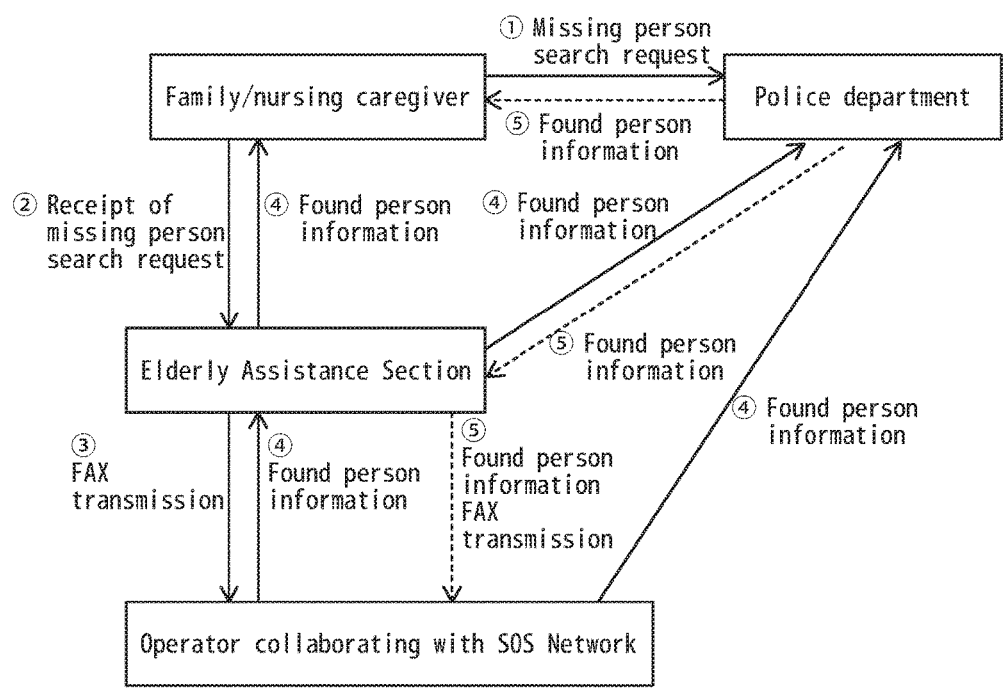
FIG. 9 Block diagram for explaining the system of a Wanderer Monitoring SOS Network.

In this regard, with a Wanderer Monitoring SOS Network such as that shown in FIG. 9, it is hard to expect as a practical matter that service could be provided 24 hours per day 365 days per year, and there is the fact that application to register in advance is complicated. On the other hand, with the technique of the present embodiment, through use of serial number 15 on jewelry item 10, which serves as identification marker for the user in question, by using this in such fashion that it is associated with credit card company payment information, it is possible to cause input and administration of identification information for the user to be greatly simplified and to be automated. Furthermore, because the credit card company is available 24 hours per day 365 days per year, this makes it possible to easily initiate service(s) at any time. Moreover, the credit card company of course not being the one that will be engaging in rescue operations, because the rescue organization 1200 (e.g., fire department, security company, etc.) which is the one that will be engaging in rescue operations is available 24 hours per day 365 days per year, this makes it possible, with respect to rescue as well, to easily initiate service(s) at any time.

Because the serial number 15 that is used on jewelry item 10 can be one that conforms to specifications for proof of product authenticity, extended product warranty, or the like, so long as serial number 15 and identification information 1550 are such that they can be mutually associated it will also be possible to apply the present embodiment to persons who purchased jewelry item 10 prior to initiation of rescue services. Moreover, with jewelry item 10 having serial number 15, usage of rescue service(s) in accordance with the present embodiment is not limited only to companies related to the present inventor(s) but may spread to other companies as well. Note that there is of course no objection to introduction of a new serial number 15 such as might permit more effective application of rescue service(s) (rescue method(s)/rescue system(s)) in accordance with the present embodiment.

Furthermore, because the technique of the present embodiment uses serial number 15 of jewelry item 10, unlike the situation with tracking and monitoring of the person in question by electronic equipment (PHS, mobile telephones, smartphones, etc.), it is advantageous in that the problem of depleted batteries does not occur. Moreover, because GPS functionality is not being used to constantly monitor the location of the person in question 1000, this reduces stress on the person in question 1000, this being one advantage that should encourage widespread use of the technique of the present embodiment. In addition, because the person in question can purchase the jewelry item 10 that he or she likes, this is also a benefit from the standpoint that this will increase the likelihood that it will be worn on a regular basis.

Moreover, unlike the situation with the Wanderer Monitoring SOS Network, the technique of the present embodiment may also be applied to healthy adults, and when rescue service(s) in accordance with the present embodiment are utilized, complicated application for registration with a municipality is unnecessary, the fact that all a user 1000 need do is purchase jewelry item 10 having serial number 15 and wear it being a significant advantage.

In light of arrangements for dispatch of ambulances, the response by police to a request to conduct a missing person search, and so forth, it would be beneficial if the rescue method/system (wandering person care method/system) associated with embodiment(s) of the present invention were adopted by entities including municipalities. However, it may be that it will take time for all municipalities nationwide to reach the point where they are willing to cooperate in the rescue method/system of the present embodiment, or it may be that there are municipalities who choose not to cooperate toward such nationwide adoption. Taking this into account, it is preferred that the focus primarily be on private-sector companies, that reliance on cooperation from municipalities be kept to a minimum, and that as little load as possible be placed on public infrastructure.

Figure 7:
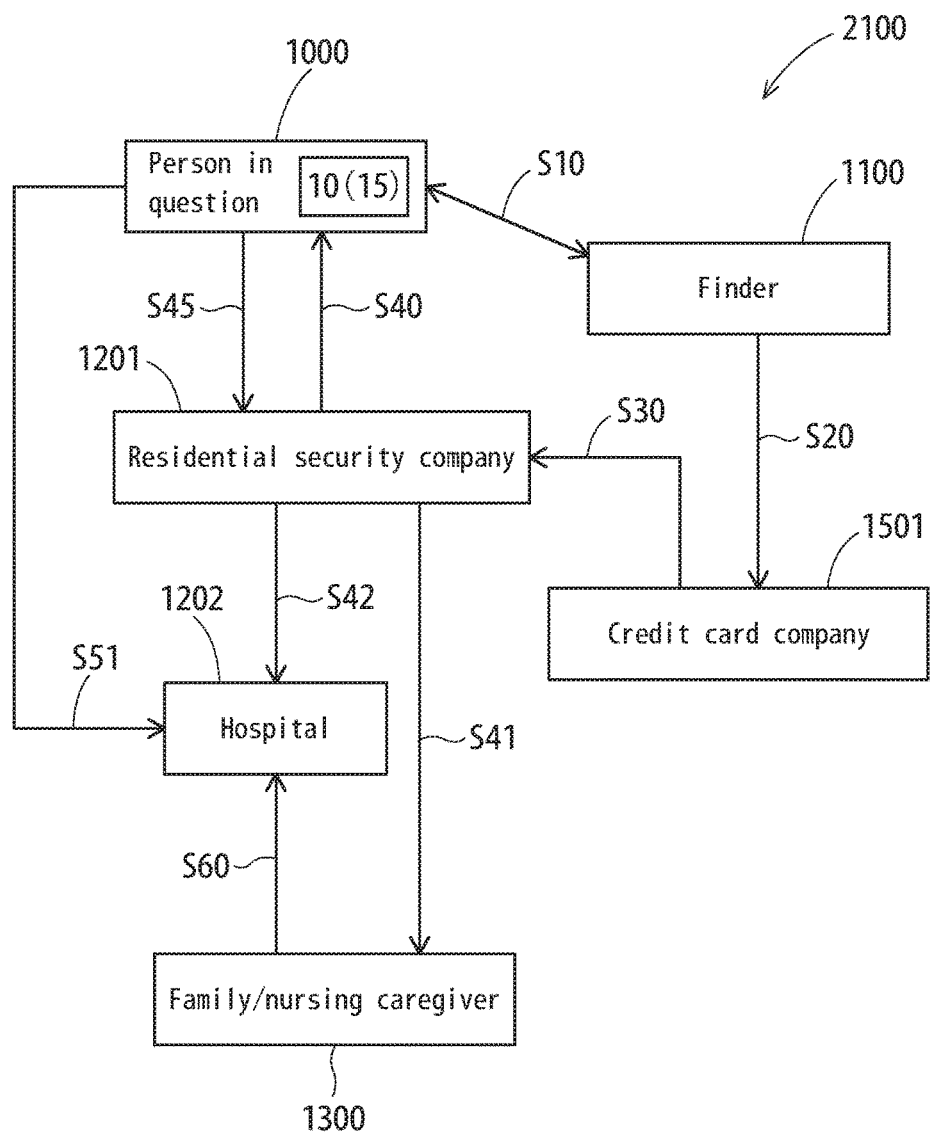
FIG. 7 Block diagram for explaining an example of a rescue method associated with an embodiment of the present invention.

FIG. 7 is an example of a rescue method/system constituted in accordance with an embodiment of the present invention in which the focus is primarily on private-sector companies. FIG. 7 is a block diagram for explaining a rescue method/system associated with the present embodiment in accordance with this example, being in basic terms similar to FIG. 3. Description that would be duplicative in light of the description given with respect to FIG. 3 will therefore be omitted.

At the rescue method/system shown in FIG. 7, data management company 1500 is a credit card company 1501. There is no objection to a situation in which this credit card company 1501 is a group consisting of a plurality of credit card companies 1501 capable of processing payment for jewelry item 10. In addition, based on serial number 15 of jewelry item 10, credit card company 1501 transmits identification information 1550 to residential security company 1201 which is a rescue organization (see step S30).

Because residential security company 1201 provides security services 24 hours per day 365 days per year, introduction, administration and management, and implementation of the rescue method/system of the present embodiment is easy. Because residential security company 1201 patrols the area of its jurisdiction by automobile, bicycle, and motorcycle, and/or the like, rescue of the person in question 1000 is easy. In this regard, while a convenience store or the like may also be a rescue organization 1200, considering its ability to mobilize to rescue the person in question 1000, residential security company 1201 is better able to deliver benefit.

When the person responsible at residential security company 1201 rescues person in question 1000, if there is a need to go to hospital 1202 the following may be carried out. First, where the person in question 1000 is unconscious or is having a seizure or the like, because an ambulance will be required to move the person in question 1000, residential security company 1201 arranges to have an ambulance dispatched (or contacts the finder by telephone and has him or her arrange in advance to have an ambulance dispatched).

Where it possible to determine that the person in question 1000 is conscious and healthy but not possible to determine who the person in question is, the person responsible at residential security company 1201 may, instead of calling an ambulance, bring the person in question to the location of family/nursing caregiver 1300. At such time, if it is thought that to be on the safe side it is best to bring the person in question to hospital 1202, residential security company 1201 first contacts the hospital (arrow S42) and then brings the person in question to hospital 1202. In addition, residential security company 1201 contacts family/nursing caregiver 1300 (arrow S41), and has them come to hospital 1202 (arrow S60).

It is thus possible to operate rescue service(s) in accordance with the present embodiment in such manner that load on municipalities, including ambulances thereof, is kept as low as possible, and the focus is primarily on private-sector companies.

Figure 8:
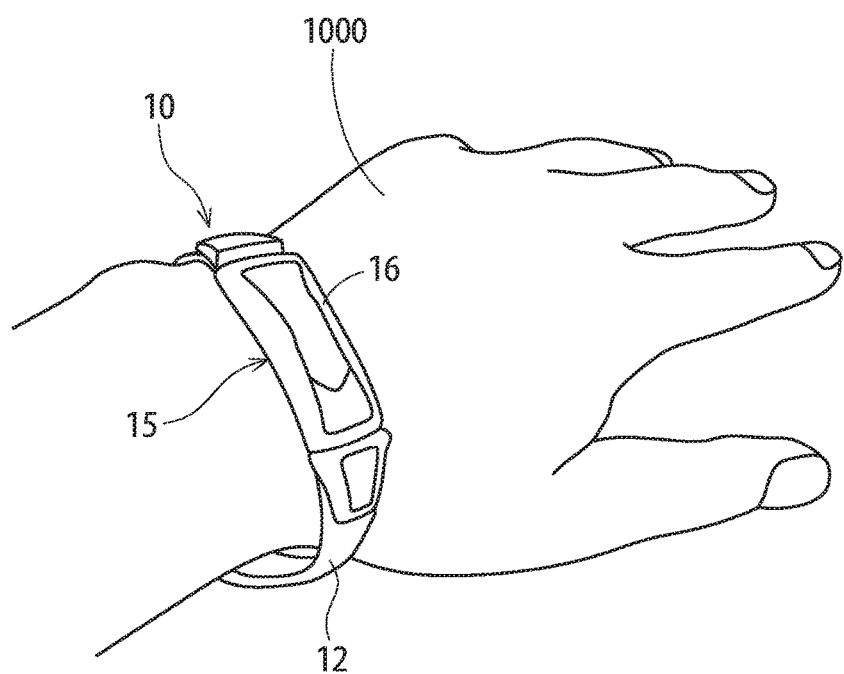
FIG. 8 Drawing showing in schematic fashion a jewelry item (bracelet) 10 associated with an embodiment of the present invention.

Whereas the foregoing embodiments have been described in terms of a situation in which the necklace shown in FIG. 1 was used as jewelry item 10, jewelry item 10 is not limited to necklaces. Jewelry item 10 might, for example, be a bracelet such as is shown in FIG. 8. Furthermore, there is no objection to employment of a jewelry item 10 that is an anklet which is worn about the ankle.

Note that while "jewelry item 10" of the present embodiment primarily refers to an item that can be worn on one's body (necklace, bracelet, anklet, etc.), it may also be a decorative item that may be worn on one's person or an accessory item mainly used as supplement to clothing that is worn. More specifically, so long as it is a jewelry item (decorative item or accessory item) having a serial number 15, these may include watches, rings, earrings, broaches, handbags, shoes, and so forth.

Furthermore, the present embodiment was described in terms of an example in which smartphone 20 was employed as mobile communication equipment, and while it is often the case that a mobile telephone may be employed, it is also possible depending on the situation to employ a tablet computer, laptop computer, or wearable computer (e.g., a smartwatch such as an Apple Watch manufactured by Apple Inc., Google glass manufactured by Google Inc., etc.).

While the present invention has been described above in terms of preferred embodiments, such descriptions should not be construed as limitations, many modifications thereof being of course possible. For example, modification is possible such that security company (residential security company) 1201 also operates data management company 1500. Furthermore, program(s) (especially rescue app 25 installed at smartphone 20) of embodiments associated with the present invention may be separately commercialized as intellectual property. Moreover, while it was contemplated in the present embodiment that the person in question (user) 1000 was a human being, as the tendency to treat pets as family has grown widespread, there is no prohibition against employing a pet as user 1000 and causing said jewelry item 10 to be worn by the pet so that it may be used for identification of the pet.

INDUSTRIAL UTILITY

The present invention makes it possible to provide a rescue method and rescue system (and wandering person care method and system) permitting easy identification of personal information.

EXPLANATION OF REFERENCE NUMERALS

10 Jewelry item (necklace or bracelet)
12 Linear member (wire)
14 Connector (catch)
15 Serial number
16 Pendant
20 Smartphone (mobile communication terminal)
21 Display
25 Icon (rescue app icon)
29 Camera
1000 User (person in question)
1100 Finder
1200 Rescue organization
1210 User rescue database
1300 Family/nursing caregiver 1500 Data management company
1510 Identification information database
1550 Identification information
1900 Communication network

The invention claimed is:

1. A rescue system for identifying and rescuing a person in question, the rescue system comprising:
   a first database that stores a serial number on a jewelry item as identification information; and
   a second database that receives user rescue information including the identification information by way of a communication network;
   wherein the first database is provided at a data management company;
   the second database is provided at a rescue organization;
   the serial number is transmitted to the first database by a mobile communication device; and
   incorporated within the second database is rescue programming for issuing a command to rescue the person in question based on the user rescue information.

2. The rescue system according to claim 1 wherein
   the jewelry item has a form such as will permit wearing thereof by the person in question; and
   the jewelry item is one species selected from among the group consisting of necklace, bracelet, and anklet.

3. The rescue system according to claim 1, wherein
   the rescue organization is at least one species selected from among the group consisting of fire department, police department, and security company; and
   the user rescue information includes the identification information and includes location information pertaining to the person in question.

4. The rescue system according to claim 1, wherein
   the mobile communication device is a mobile communication terminal possessing GPS functionality for obtaining location information;
   location information pertaining to the user is transmitted to the data management company based on location information obtained by the GPS functionality possessed by the mobile communication terminal.

5. The rescue system according to claim 1, wherein the serial number is a two-dimensional barcode.

6. The rescue system according to claim 1, wherein the data management company is a credit card company.

7. A care system for identifying and rescuing a wandering person, the care system comprising:
   a first database that stores a serial number on a jewelry item as identification information; and
   a second database that receives user rescue information including the identification information by way of a communication network;
   wherein the first database is provided at a data management company;
   the second database is provided at a rescue organization;
   the serial number is transmitted to the first database by a mobile communication device;
   the user rescue information includes the identification information and includes location information pertaining to the wandering person; and
   incorporated within the second database is rescue and care programming for issuing a command to rescue and care for the wandering person.

8. The care system according to claim 7, wherein
   the jewelry item has a form such as will permit wearing thereof by the person in question;
   the jewelry item is one species selected from among the group consisting of necklace, bracelet, and anklet; and
   the rescue organization is at least one species selected from among the group consisting of fire department, police department, and security company.

9. A rescue method for identifying and rescuing a person in question,
   the rescue method being executed using a rescue system comprising
      a first database that stores a serial number on a jewelry item as identification information; and
      a second database that receives user rescue information including the identification information by way of a communication network; and
   the rescue method including
      an operation in which a user wearing the jewelry item having the serial number is encountered and the serial number on said jewelry item is recognized;
      an operation in which the serial number is conveyed to a data management company that stores the serial number as identification information pertaining to the user;
      an operation in which the identification information pertaining to the user is conveyed from the data management company to a rescue organization capable of rescuing the user; and
      an operation in which a command to rescue the user is issued at the rescue organization;
   wherein the first database in which the serial number of the jewelry item is stored is provided at the data management company;
   the first database is connected to the communication network;
   a mobile communication terminal is used at the operation in which the serial number is conveyed;
   the second database that receives the identification information is provided at the rescue organization; and
   the second database is used at the operation in which the command to rescue the user is issued.

10. The rescue method according to claim 9, wherein
   the jewelry item at the operation in which the recognition occurs is one species selected from among the group consisting of necklace, bracelet, and anklet;
   at the operation in which the recognition occurs, the serial number is recognized by the mobile communication terminal possessed by the finder who encountered the user;
   the data management company is a credit card company;
   the serial number recognized by the mobile communication terminal of the finder is transmitted to the credit card company by the communication network connected to the mobile communication terminal;
   the mobile communication terminal possesses GPS functionality for obtaining location information;
   location information pertaining to the user is transmitted to the credit card company based on the location information of the GPS functionality possessed by the mobile communication terminal of the finder;
   the rescue organization is at least one species selected from among the group consisting of fire department, police department, and security company;
   the identification information pertaining to the user includes the location information of the person in question; and
   incorporated within the second database is rescue programming for issuing a command to rescue the user.

11. A rescue method for identifying and rescuing a person in question, the rescue method being executed using a rescue system comprising
  a first database that stores a serial number on a jewelry item as identification information; and
  a second database that receives user rescue information including the identification information by way of a communication network; and
the rescue method including
  an operation in which a user wearing the jewelry item having the serial number is encountered and the serial number on said jewelry item is recognized;
  an operation in which the serial number is conveyed to a data management company that stores the serial number as identification information pertaining to the user;
  an operation in which the identification information pertaining to the user is conveyed from the data management company to a rescue organization capable of rescuing the user; and
  an operation in which a command to rescue the user is issued at the rescue organization;
wherein the first database is provided at the data management company; and
the second database is provided at the rescue organization.

12. The rescue method according to claim 11, wherein
the jewelry item at the operation in which the recognition occurs is one species selected from among the group consisting of necklace, bracelet, and anklet;
at the operation in which the recognition occurs, the serial number is recognized by a smartphone possessed by the finder who encountered the user;
the data management company is a credit card company; and
the serial number recognized by the smartphone of the finder is transmitted to the credit card company by the communication network connected to the smartphone.

13. The rescue method according to claim 12, wherein location information pertaining to the user is transmitted to the credit card company based on location information possessed by the smartphone of the finder.

14. The rescue method according to claim 12, wherein
the serial number is recognized by a camera of the smartphone of the finder; and
stored at the smartphone of the finder is a rescue application that transmits the serial number to the credit card company.

15. The rescue method according to claim 11, wherein
at least one member of the rescue organization is a security company; and
an instruction to go to the location of the user is issued to staff of the security company based on user rescue information including the identification information pertaining to the user from the data management company.

16. The rescue method according to claim 11, wherein
at least one member of the rescue organization is a fire department having an ambulance; and
an instruction to go to the location of the user is issued to staff of the fire department based on user rescue information including the identification information pertaining to the user from the data management company.

17. The rescue method according to claim 11, wherein the serial number is a two-dimensional barcode.

18. A method for identifying and caring for a wandering person,
the wandering person care method being executed using a care system comprising
  a first database that stores a serial number on a jewelry item as identification information; and
  a second database that receives user rescue information including the identification information by way of a communication network; and
the wandering person care method including
  an operation in which a wandering person wearing the jewelry item having the serial number is encountered and the serial number on said jewelry item is recognized;
  an operation in which the serial number is conveyed to a data management company that stores the serial number as identification information pertaining to the wandering person;
  an operation in which the identification information pertaining to the wandering person is conveyed from the data management company to a rescue organization that will rescue and care for the wandering person; and
  an operation in which a command to care for and rescue the wandering person is issued at the rescue organization;
wherein the first database is provided at the data management company; and
the second database is provided at the rescue organization.

19. The wandering person care method according to claim 18, wherein
the jewelry item at the operation in which the recognition occurs is one species selected from among the group consisting of necklace, bracelet, and anklet; and
the jewelry item is equipped with a catch.

20. The wandering person care method according to claim 18, wherein
at the operation in which the recognition occurs, the serial number is recognized by a smartphone possessed by the finder who encountered the wandering person;
the data management company is a credit card company; and
the serial number recognized by the smartphone of the finder is transmitted to the credit card company by the communication network connected to the smartphone.

21. The wandering person care method according to claim 20, further comprising an operation in which an advertisement of the credit card company is caused to be displayed at a plurality of smartphones connected to the communication network.

22. A program for identifying and rescuing a person in question that causes execution of a rescue method for identifying and rescuing the person in question,
the rescue method being executed using a rescue system comprising
  a first database that stores a serial number on a jewelry item as identification information; and
  a second database that receives user rescue information including the identification information by way of a communication network; and
the program for identifying and rescuing the person in question being a program that causes
  a step in which a user wearing the jewelry item having the serial number is encountered and the serial number on said jewelry item is recognized;
  a step in which the serial number is conveyed to a data management company that stores the serial number as identification information pertaining to the user;

a step in which the identification information pertaining to the user is conveyed from the data management company to a rescue organization capable of rescuing the user; and a step in which a command to rescue the user is issued at the rescue organization to be executed in the context of the rescue system;

the program for identifying and rescuing the person in question being such that the first database is provided at the data management company; and the second database is provided at the rescue organization.

23. An application program capable of being executed by a mobile communication terminal used in the context of the program for identifying and rescuing the person in question according to claim 22, the application program being such that, of the steps in the program for identifying and rescuing the person in question, the step in which the serial number of the jewelry item is recognized and the step in which the serial number is conveyed to the data management company are executed by the mobile communication terminal.

* * * * *